United States Patent
Foos et al.

(10) Patent No.: US 10,568,711 B2
(45) Date of Patent: Feb. 25, 2020

(54) PHARMACEUTICAL WASTE DISPOSAL SYSTEM

(71) Applicant: Stericycle, Inc., Northbrook, IL (US)

(72) Inventors: Brian S. Foos, Roselle, IL (US); Gerry VanDomelen, Eagan, MN (US)

(73) Assignee: STERICYCLE, INC., Bannockburn, IL (US)

( * ) Notice: Subject to any disclaimer, the term of this patent is extended or adjusted under 35 U.S.C. 154(b) by 470 days.

(21) Appl. No.: 15/477,663

(22) Filed: Apr. 3, 2017

(65) Prior Publication Data

US 2018/0071046 A1  Mar. 15, 2018

Related U.S. Application Data

(60) Provisional application No. 62/393,239, filed on Sep. 12, 2016.

(51) Int. Cl.
| | |
|---|---|
| *A61B 50/36* | (2016.01) |
| *G06Q 10/00* | (2012.01) |
| *A61B 90/96* | (2016.01) |
| *A61B 50/00* | (2016.01) |

(52) U.S. Cl.
CPC .............. *A61B 50/36* (2016.02); *A61B 90/96* (2016.02); *G06Q 10/30* (2013.01); *A61B 2050/0067* (2016.02); *Y02W 90/20* (2015.05)

(58) Field of Classification Search
CPC . A61B 50/36; A61B 90/96; A61B 2050/0067; G06Q 10/30; Y02W 90/20
USPC ....................................................... 588/300
See application file for complete search history.

(56) References Cited

U.S. PATENT DOCUMENTS

| | | | |
|---|---|---|---|
| 5,972,291 A | 10/1999 | Healy et al. | |
| 7,533,028 B2 | 5/2009 | Mallett et al. | |
| 7,533,029 B2 | 5/2009 | Mallett et al. | |
| 8,336,129 B2 | 12/2012 | Mullowney | |
| 8,348,056 B2 | 1/2013 | Maness | |
| 8,450,389 B1 | 5/2013 | Barefoot | |
| 8,534,459 B2 | 9/2013 | Maness | |
| 8,785,712 B2 | 7/2014 | Deryck et al. | |
| 8,821,363 B1 | 9/2014 | Barefoot | |
| 9,005,098 B2 | 4/2015 | Ziemba | |
| 9,035,121 B1 | 5/2015 | Goodsell et al. | |
| 9,044,377 B2 | 6/2015 | Maness | |
| 9,242,282 B2 | 1/2016 | Mullowney et al. | |
| 9,302,134 B1 | 4/2016 | Nelson et al. | |
| 2004/0144682 A1 | 7/2004 | Altmayer | |
| 2006/0253297 A1* | 11/2006 | Mallett | ............ A61L 11/00 209/702 |
| 2012/0088951 A1 | 4/2012 | Deryck et al. | |
| 2013/0232917 A1 | 9/2013 | Dueñas Sanchez | |
| 2014/0187842 A1 | 7/2014 | Holaday et al. | |
| 2014/0235917 A1 | 8/2014 | Best | |
| 2015/0231433 A1 | 8/2015 | Short | |
| 2015/0231673 A1 | 8/2015 | Dallas et al. | |
| 2016/0008860 A1 | 1/2016 | Dallas et al. | |

OTHER PUBLICATIONS

Medline Patents, <http://www.medline.com/media/mkt/pdf/Medline-Patents-03JUN2016.pdf> published Jun. 3, 2016 (4 pages).
EM Innovations, <http://www.ems1.com/ems-products/Infection-Control/press-releases/2019727-EM-Innovations-Introduces-Drug-Dispose-All-The-Choice-for-Safe-Drug-Disposal/> published Nov. 10, 2014 (7 pages).
Health Care Logistics, Inc., <http://healthcarelogistics.cc/old-blog/drug-dispose-all-protects-against-the-dangers-of-expired-and-unused-drugs> published Jun. 11, 2015 (2 pages).

* cited by examiner

*Primary Examiner* — Edward M Johnson
(74) *Attorney, Agent, or Firm* — Michael Best & Friedrich LLP

(57) ABSTRACT

A waste container includes a neck defining an opening through which waste can be inserted into the waste container, and an insert snap-fit into the opening. The insert has an engagement portion engaged with the neck to secure the insert into the opening, and a body portion having a plurality of differently-sized apertures for allowing passage of waste through the insert and into the waste container.

20 Claims, 5 Drawing Sheets

PHARMACEUTICAL WASTE DISPOSAL SYSTEM

RELATED APPLICATIONS

This application claims the benefit of U.S. Provisional Patent Application No. 62/393,239 filed Sep. 12, 2016, the entire content of which is hereby incorporated by reference herein.

BACKGROUND

The present invention relates to waste disposal systems, and more particularly to disposal systems for safely disposing of pharmaceuticals and controlled substances such as pills, liquids, capsules, patches, and other related waste items.

At present, many hospitals, clinics and other healthcare facilities dispose controlled substance medical waste into the sink or toilet, often in direct conflict with environmental regulations. The costs associated with environmentally responsible pharmaceutical and controlled substance waste disposal can be prohibitive. Thus, there is a need for a practical, safe, secure, and cost efficient method for healthcare facilities to dispose of controlled substance and pharmaceutical waste.

SUMMARY

In one embodiment, the invention provides a system for the disposal and transportation of waste. The system includes a box, a waste container sized and configured to fit within the box for (i) delivery to a user prior to the waste container receiving pharmaceutical waste, and (ii) for shipment to a disposal provider after the waste container has received pharmaceutical waste. The system further includes a deactivating agent operable to react with and neutralize waste placed in the waste container, and a solidifying agent packaged separately from the waste container such that after pharmaceutical waste has been placed in the waste container and neutralized by the deactivating agent, the solidifying agent can be placed into the waste container to solidify contents of the waste container. The box has affixed thereto a shipping label addressed to the disposal provider such that after the solidifying agent has been added to the waste container, a user can place the waste container into the box and send it directly to the disposal provider by U.S. mail or shipping courier.

In another embodiment, the invention provides a method of using a waste disposal and transportation system. The method includes receiving a parcel containing a box having a shipping label affixed thereto, the shipping label addressed to a disposal provider, a waste container, a deactivating agent, and a solidifying agent. Further method steps include removing the box from the parcel, removing the waste container from within the box, saving the box for later use in returning the waste container to the disposal provider, adding water to the waste container to activate the deactivating agent, placing pharmaceutical waste into the waste container to be neutralized by the deactivating agent, placing the solidifying agent into the waste container to solidify neutralized contents of the waste container, sealing the waste container, placing the sealed waste container back into the saved box, closing the box to retain the waste container therein, and sending the box directly to the disposal provider using the affixed shipping label.

In yet another embodiment the invention provides a waste container including a neck defining an opening through which waste can be inserted into the waste container, and an insert snap-fit into the opening. The insert has an engagement portion engaged with the neck to secure the insert into the opening, and a body portion having a plurality of differently-sized apertures for allowing passage of waste through the insert and into the waste container.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
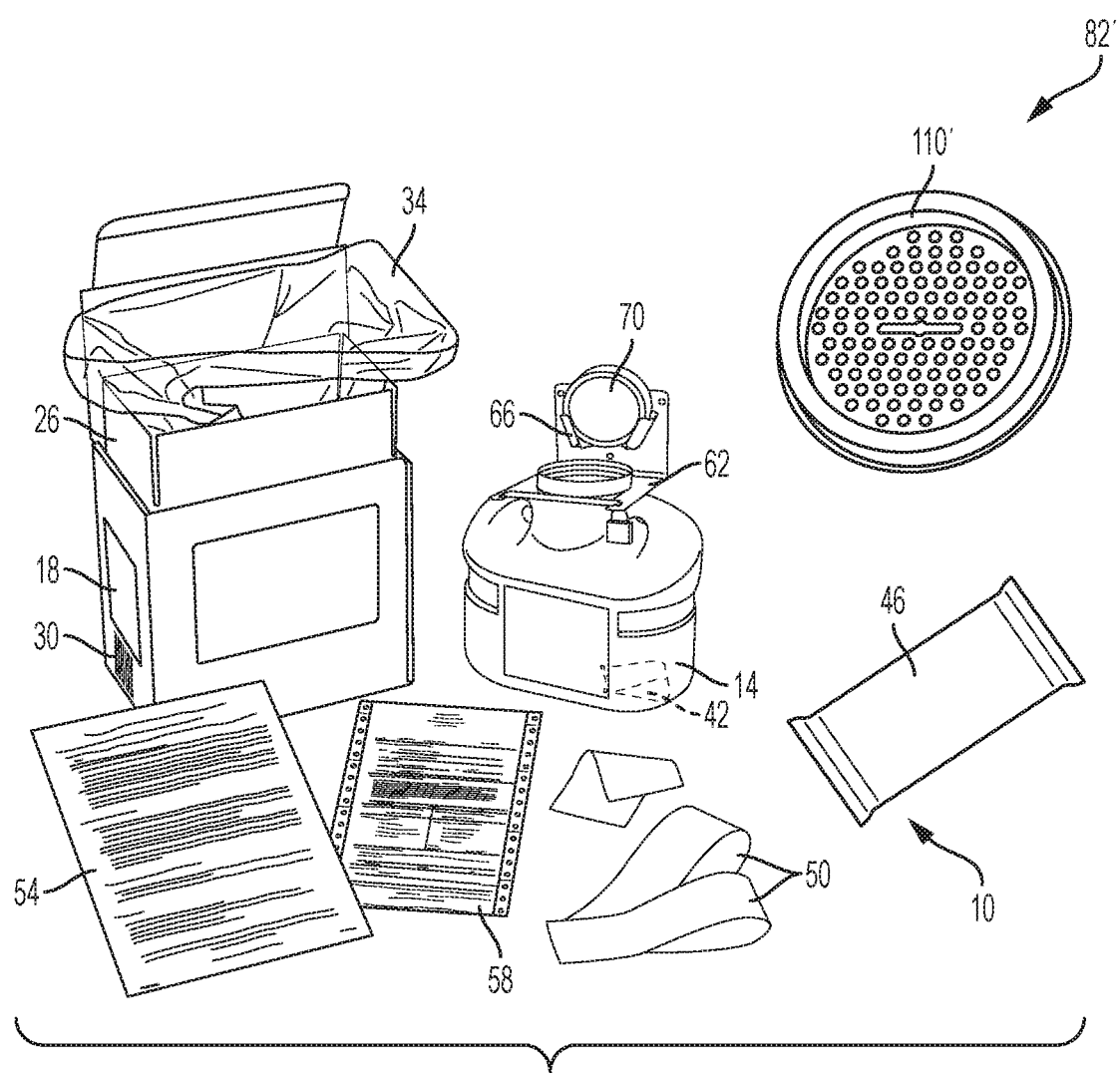
FIG. 1 illustrates a system embodying the invention for the disposal and transportation of waste.

The present invention provides a mail-back or ship-back controlled substance denaturing system in the form of a kit 10. FIG. 1 provides an overview of the system, which provides a safe and secure solution to disposing of controlled substances, typically in the form of pills, capsules, liquids, and patches. The waste disposal kit 10 or system can be packed in a single parcel (not shown) for convenient delivery/shipment to the user. Inside the parcel, the kit 10 includes a waste container 14 that can be filled with controlled substance waste and secured for return shipment by the healthcare facility or end user to the waste management service/disposal provider.

In addition to the waste container 14, the kit 10 includes a return shipping box 18 in which the waste container 14 may be placed for delivery to the user inside the parcel. In other embodiments, the return shipping box 18 could be provided separately from the waste container 14 in a folded or otherwise collapsed configuration in the parcel for delivery to the user. After the waste container 14 is filled and readied for return as described below, the folded return shipping box 18 can be constructed to receive the waste container 14 for convenient return to the disposal provider. The return shipping box 18 has affixed thereon a shipping label 22 (see FIG. 3D) that is addressed to the waste disposal provider to facilitate easy and hassle-free return shipping directly to the disposal provider. In a preferred embodiment, the shipping label 22 is pre-paid for shipment to the disposal provider. Examples of shipping labels include postage-paid mailing labels from the Unites States Post Office or pre-paid labels for shipping couriers such as FedEx, UPS, DHL, or other comparable couriers. The box 18 can include an inner liner or inner box 26 to provide for dual-layer strength and protection (see the white outer box 18 and the brown inner liner or inner box 26 in FIG. 1). Bar-coding 30 or other similar identification schemes (e.g., QR codes) can also be placed on the outside of the box 18 to assist the disposal provider in tracking the box 18 and/or providing information regarding the user who returned the waste for disposal.

The kit 10 can also include a plastic bag 34 and closure 38 (e.g., twist-tie, clip, or other similar closure) that can enclose the waste container 14 within the box 18, both when originally delivered to the user and for return shipping to the disposal provider. The plastic bag 34 assists with making the kit leak-proof for both original shipment to the user and return shipment to the disposal provider.

The kit 10 also includes a drug deactivating or denaturing agent 42. In a preferred embodiment, the deactivating agent 42 is provided in one or more dissolvable packets and is originally housed within the waste container 14. In other embodiments, the deactivating agent 42 may be provided separately from the waste container 14 and can be placed into the waste container 14 by the user prior to use. The number of dissolvable packets containing the deactivating agent 42 can vary depending on the volume of the waste container 14. The illustrated waste container 14 is a one-gallon size, however other kits 10 provide larger waste containers (e.g., 3 gallon or other sizes). Typically, activated carbon is used as a chemical deactivating or denaturing agent 42, which adsorbs (i.e., binds) the controlled waste substance. In the illustrated embodiment, the deactivating agent 42 is available from Verde Technologies, Inc. of Burnsville, Minn. as its "MEDSAWAY" product, and is covered by one or more of U.S. Pat. Nos. 8,979,724; 8,535,711; and 8,475,837.

The kit 10 further includes a solidifying agent 46 that is packaged separately from both the waste container 14 and the deactivating agent 42. The solidifying agent 46 is available from Safetec of America, Inc. of Buffalo, N.Y. as its "Green-Z"® product. As will be described below, the solidifying agent 46 is added to the container 14 after the container 14 has been filled with waste and is ready to be shipped to the disposal provider. The solidifying agent 46 can be provided in a bag, pouch, or other container that can be stored separately from the waste container 14 (perhaps with the box 18) and later opened for pouring into the waste container 14.

Also included in the kit 10 are tape strips 50 that can be used to close and secure the box 18 for return shipment to the disposal provider. Of course, the user can use additional tape as desired. The kit 10 can also include the user guides 54 to instruct the user on how to properly use the kit 10. Finally, the kit 10 can include any required tracking documents 58 to comply with U.S. Drug Enforcement Administration security requirements (or similar documentation required in foreign jurisdictions).

Figure 2:
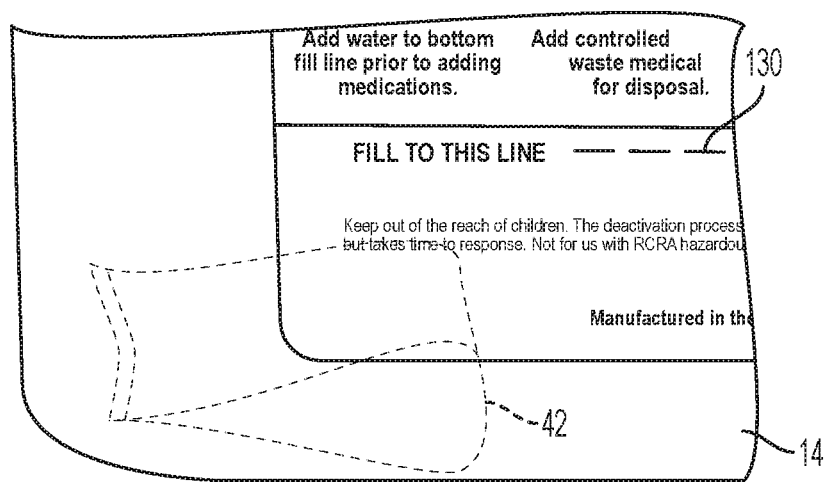
FIG. 2 is a partial, enlarged view of the waste container shown in FIG. 1.

As mentioned, the waste container 14 can come in a variety of sizes (e.g., 1 gallon, 3 gallon, etc.) and in the illustrated embodiment is a blow-molded plastic container. As shown in FIGS. 1 and 2, a mounting bracket 62 can be coupled to the waste container 14 for securing/hanging the waste container 14 on a wall. The illustrated mounting bracket 62 further includes a feature 66 for holding the cover 70 of the waste container 14, which is not used during waste collection. Once the waste has been collected and solidified, the cover 70 can then be placed on the waste container 14 to seal the waste container 14 for shipment to the disposal provider. In other embodiments, the bracket 62 may not be included.

Figure 4:
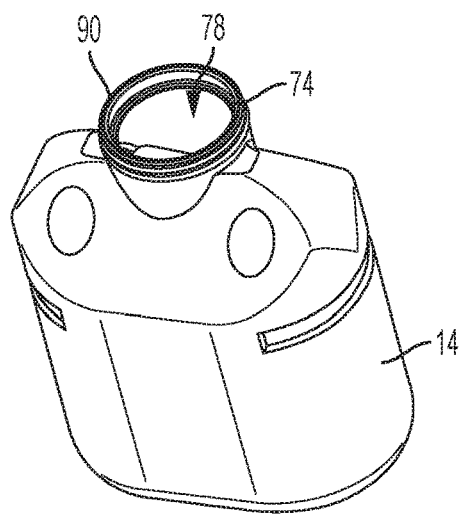
FIG. 4 is a perspective view of the waste container.
Figure 5:
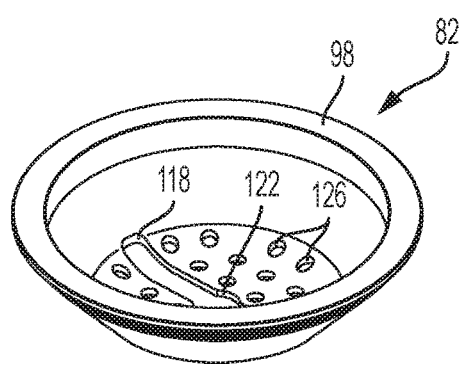
FIG. 5 is a perspective view of a snap-in insert for use with the waste container.
Figure 6:
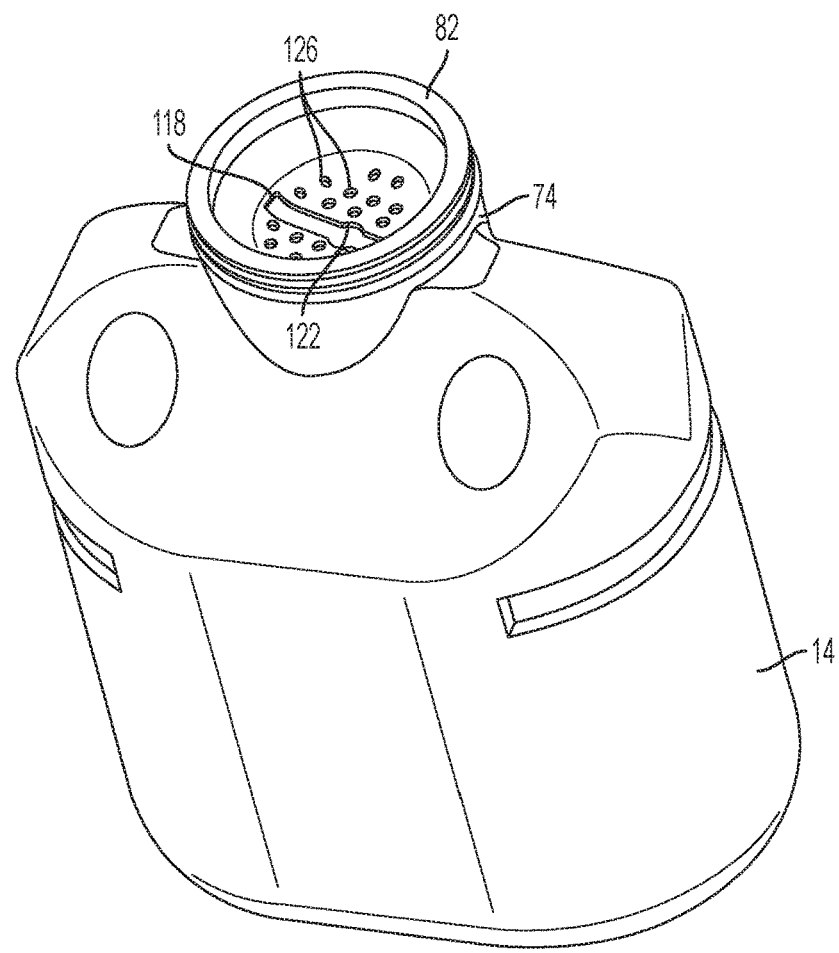
FIG. 6 is an assembled view of the waste container with the snap-in insert.
Figure 7:
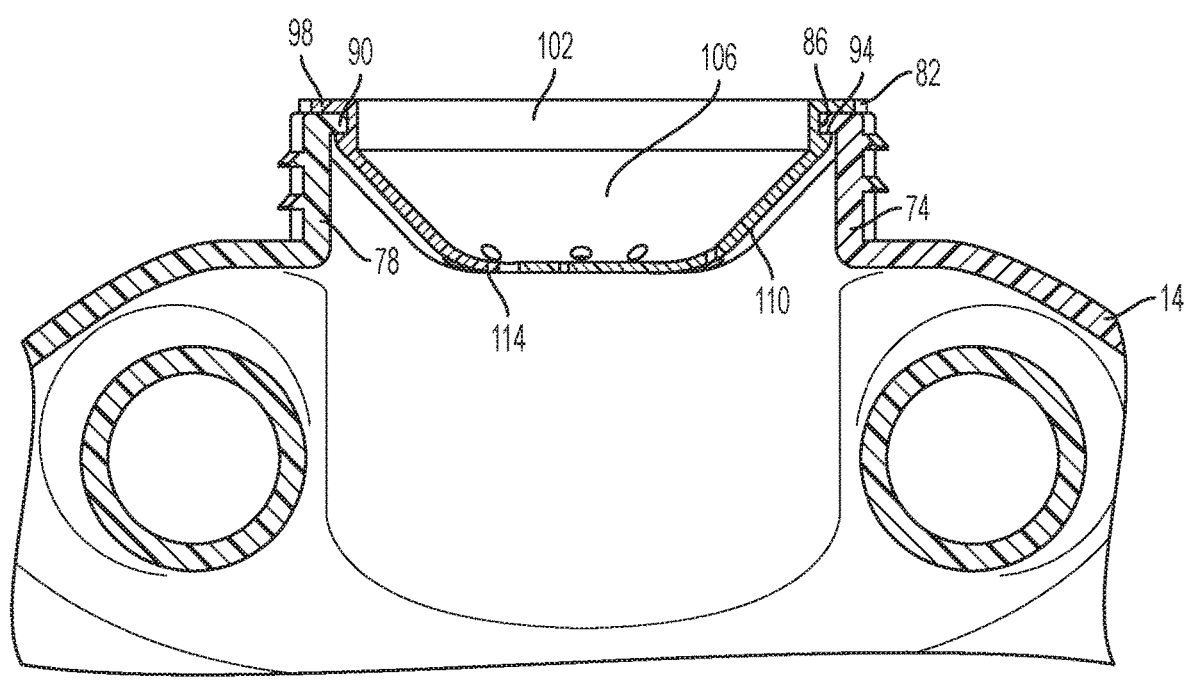
FIG. 7 is a section view of the snap-in insert positioned in the neck of the waste container.

FIGS. 4-7 illustrate the waste container 14 in detail. As seen in FIG. 4, the waste container 14 includes a neck 74 that defines an opening 78 to the interior of the waste container 14. The illustrated neck 74 is threaded on the outside to receive the mating threads of the cover 70. FIG. 5 illustrates a snap-in insert 82 for attachment to the neck 74 to provide some level of a tortuous path into the opening 78 of the waste container 14. FIGS. 6 and 7 show the snap-in insert 82 engaged with the neck 74 over the opening 78. As best seen in FIG. 7, an annular recess 86 near the top of the insert 82 receives an annular lip 90 protruding inwardly from the neck 74 to secure the insert 82 in place over the opening 78 of the waste container 14. The provider of the kit 10 will typically place the deactivating agent packet(s) 42 into the waste container 14 and will then install the insert 82 by pressing it into the neck 74 until the annular lip 90 of the neck 74 moves past the shoulder 94 of the insert 82 and snaps into the annular recess 86. In this manner, the end user need not handle the deactivating agent 42 and the insert 82 will keep the deactivating agent 42 inside the waste container 14. The insert 82 also prevents unauthorized access to the medical waste disposed in the container 14.

The insert 82 has an upper annular flange 98 that rests on the upper surface of the neck 74. Together, the flange 98, the annular recess 86, and the shoulder 94 beneath the annular recess 86 define an engagement portion 102 configured to engage the neck 74 and secure the insert 82 onto the neck 74 and in the opening 78 of the waste container 14. The insert 82 further includes a body portion 106, which in the illustrated embodiment of FIGS. 5-7 is somewhat bowl-shaped with a sloped sidewall portion 110 and a generally planar bottom wall portion 114. A plurality of differently-sized apertures can be formed in one or both of the sidewall 110 and bottom wall 114 portions for allowing passage of waste through the insert 82 and into the waste container 14. For example, as best seen in FIGS. 5 and 6, the bottom wall portion 114 of the insert 82 includes an elongated aperture 118 that can be described as a slit or a slot that is sized and configured to receive used patches, such as medicinal Fentanyl patches. At the central or middle portion of the elongated aperture 118 is a slightly enlarged aperture portion 122 (providing a slightly larger diameter than the width of the elongated aperture) for receiving pills, capsules, and other waste that is too large to fit through the remainder of the elongated aperture 118. Furthermore, a plurality of other circular and same-sized apertures 126 are provided on either side of the elongated aperture 118 and will facilitate the passage of liquid waste through the insert 82 and into the waste container 14. In other embodiments, the size, shape, number, and location of the apertures can be varied as desired to accommodate particular types of waste. The bowl-shape facilitates pouring of liquid waste into the insert 82, where the liquid waste can then flow through any of the apertures in the insert 82 and into the waste container 14. In other embodiments, the insert 82 need not be bowl-shaped with the sloped sidewall portion 110. FIG. 1 illustrates a more cup-shaped insert 82' have a non-sloped or very slightly sloped sidewall portion 110'.

The method of using the kit 10 will now be described. With reference to FIG. 1, a user receives the original parcel (e.g., a container or box) containing the kit 10 and removes the contents of the kit 10 from that original parcel. The original parcel can be discarded. Within the white return shipping box 18 is the waste container 14, which in the preferred embodiment is enclosed in the plastic bag 34 and already contains therein the deactivating agent 42. The snap-in insert 82 will already be secured onto the neck 74 of the waste container 14 and the cover 70 will be secured to the neck 74 over the snap-in insert 82. The user can remove the plastic bag 34 and waste container 14 from the box 18, and then remove the waste container 14 from the plastic bag 34. All the other contents of the kit 10 apart from the waste container 14, including the return shipping box 18, the plastic bag 34 and its closure 38, the solidifying agent 46 the tape strips 50, the user guides 54, and any tracking documentation 58 should be saved. For example, all of the kit contents can be placed in the return shipping box 18 and stored in a dry and secure area that can be readily accessed when it is time to ship the collected waste to the disposal provider.

The waste container cover 70 is then removed and water is added to the waste container 14 up to the fill line 130 (see FIG. 2), which can be indicated on the waste container 14 with a decal, or by markings formed directly in or on the plastic waste container 14. The deactivating agent 42 that is included in the container 14, as delivered to the end user, will then react with the water, thereby activating the deactivating agent 42, to ready the container 14 for use. The waste container 14 can then be placed in a desired secure location for collection of waste. Controlled substance/pharmaceutical waste such as tablets, capsules, patches, and liquids can then be added to the container 14 for denaturing.

Figure 3A:
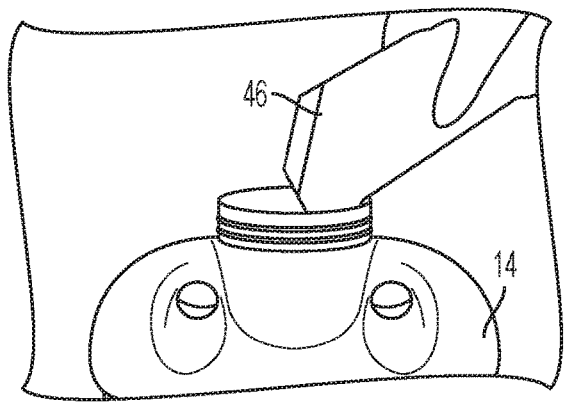
FIGS. 3A-D illustrate the procedure for securing and shipping the waste after it has been collected.
Figure 3B:
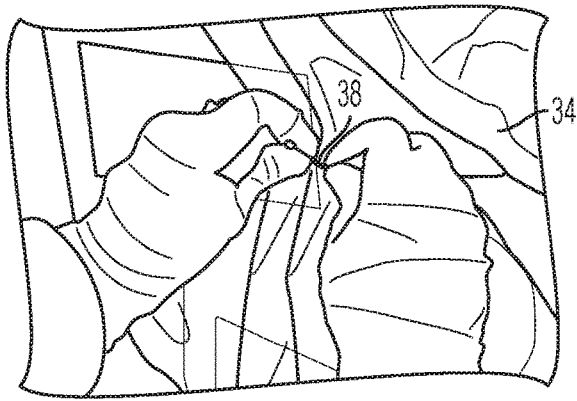
Figure 3C:
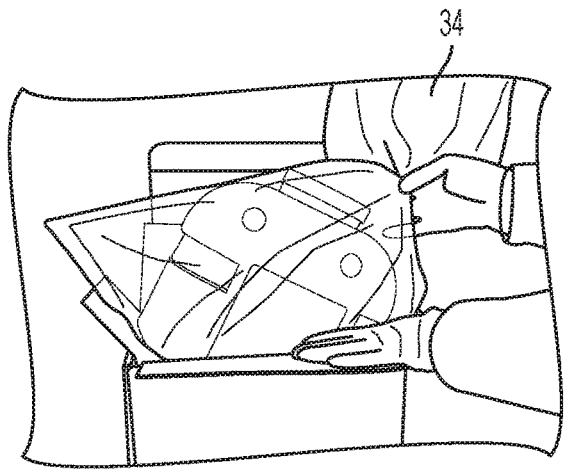
Figure 3D:
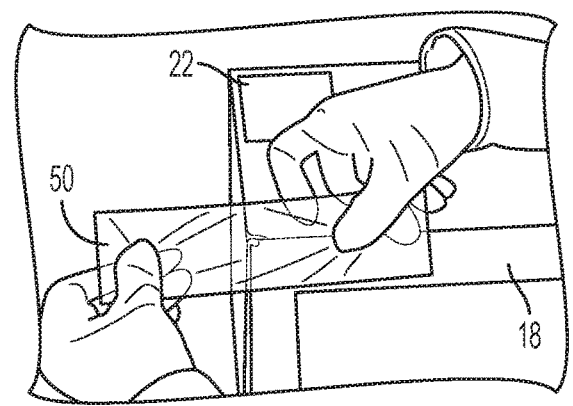

Referring now to FIGS. 3A-D, to prepare the container 14 for return to the waste management/disposal provider, the user pours the solidifying agent 46 provided with the kit 10 into the waste container 14 to harden/solidify the dissolved and neutralized waste collected in the container 14 (see FIG. 3A). The solidifying agent 46 can be poured into the waste container 14 through the elongated aperture 118 and/or central aperture 122 in the insert 82. Next, the user seals the waste container 14 by screwing the cover 70 onto the neck 74 over the snap-in insert 82. The waste container 14 is then placed back into the plastic bag 34 and the closure 38 is applied to seal the plastic bag 34 (see FIG. 3B). Next, the plastic bag 34 and enclosed waste container 14 are placed back into the return shipping box 18 (see FIG. 3C). Any security/tracking documents 58 can also be placed into the box 18. The box 18 is then closed/sealed using the provided tape strips 50 and/or additional tape (see FIG. 3D). Now the box 18 is ready to be returned for disposal. If needed, the user can complete the return-address portion of the shipping label 22, however, the shipping address is already completed on the label 22. Therefore, the user need only deliver the sealed box 18 to the appropriate pick-up location within the building (e.g., the building's mail room) or to an appropriate pick-up/drop-off location (e.g., a U.S. Post Office or courier outlet) for shipping back by mail or commercial courier to the disposal provider.

Conveniently, the cost of the kit 10 includes all of the components, the pre-paid shipping label, as well as the cost for disposing of the waste. Therefore, for a single charge, the user has an all-inclusive system for gathering, deactivating, securing, and returning the waste to the disposal provider. As used herein and in the appended claims, the "user" can be any person tasked with carrying out any of the steps described above. In some embodiments, the user might be an employee of the kit provider or the disposal provider who is on-site at the healthcare facility in which the kit 10 is being used. Attendance to the kit 10 might be part of a service offered by the kit provider or the disposal provider.

The system 10 can further include and/or be used with software that can operate with the bar-coding 30 to perform numerous functions for both the kit provider/disposal provider and the user. For example, the software is operable to provide real-time access or periodic automated reports indicating the number of kits 10 ordered by or delivered to the user, and the number of kits 10 shipped to or disposed of by the disposal provider. Various time periods (e.g., year-to-date and/or current quarter, etc.) could be reported. The user could log-into its account (e.g., using an internet-based interface) to see real-time inventory, set up periodic reporting, and place orders. Such information can be useful to both the provider and the user in determining usage, inventory, and future need. This information can also be used to drive an "auto-replenishment" function, such that the software can monitor and act when a user's supply of un-used kits 10 may be low. If desired, the user can establish an auto-replenishment order to ensure that a desired number of kits 10 are always available for use. For example, when the software determines that the user has only a predetermined number of kits 10 remaining, the software will trigger an automatic shipment and invoicing of a desired number of kits 10 to the user. Alternatively, the software could trigger an alert (e.g., and email or letter) to the user to indicate the number of remaining kits 10 and to suggest re-ordering.

Various features and advantages of the invention are set forth in the following claims.

What is claimed is:

1. A waste container comprising:
   a neck defining an opening through which waste can be inserted into the waste container; and
   an insert adapted to be positioned in the opening, the insert having an engagement portion adapted to engage the neck to secure the insert into the opening, and a body portion having a plurality of differently-sized apertures for allowing passage of waste through the insert and into the waste container.

2. The waste container of claim 1, wherein the insert is adapted to snap-fit into the neck.

3. The waste container of claim 1, wherein the insert is bowl-shaped.

4. The waste container of claim 3, wherein the body portion includes a sloped sidewall portion and a bottom wall portion.

5. The waste container of claim 1, wherein one of the plurality of apertures is elongated to receive a pharmaceutical patch.

6. The waste container of claim 5, wherein the elongated aperture includes an enlarged aperture portion formed at approximately a middle of the elongated aperture.

7. The waste container of claim 1, wherein one of the plurality of apertures is circular.

8. The waste container of claim 1, wherein the plurality of differently-sized apertures includes multiple apertures having the same shape and size, and at least one elongated aperture.

9. The waste container of claim 1, wherein the engagement portion of the insert includes an annular recess, and wherein the neck includes an inwardly-extending annular lip adapted to be received in the annular recess to secure the insert in the opening.

10. The waste container of claim 9, wherein the insert further includes an annular flange that rests on an upper surface of the neck when the annular lip of the neck is received in the annular recess of the insert.

11. The waste container of claim 1, further comprising a cover configured to be secured to the neck over the insert.

12. The waste container of claim 1, further comprising a deactivating agent positioned within the container.

13. The waste container of claim 12, further comprising indicia indicative of a fill line to which water should be added to the container, through the insert in the opening, to actuate the deactivating agent for use.

14. A waste container comprising:
a neck defining an opening through which waste can be inserted into the waste container; and
an insert adapted to be positioned in the opening, the insert having an engagement portion adapted to snap-fit into the neck to secure the insert into the opening, and a bowl-shaped body portion with a sloped sidewall portion and a bottom wall portion, the body portion having a plurality of differently-sized apertures for allowing passage of waste through the insert and into the waste container, at least one of the plurality of apertures being elongated to receive a pharmaceutical patch.

15. The waste container of claim 14, wherein the at least one elongated aperture includes an enlarged aperture portion formed at approximately a middle of the elongated aperture.

16. The waste container of claim 14, wherein the plurality of differently-sized apertures includes multiple apertures having the same shape and size.

17. The waste container of claim 14, wherein the engagement portion of the insert includes an annular recess, and wherein the neck includes an inwardly-extending annular lip adapted to be received in the annular recess to secure the insert in the opening.

18. The waste container of claim 17, wherein the insert further includes an annular flange that rests on an upper surface of the neck when the annular lip of the neck is received in the annular recess of the insert.

19. The waste container of claim 14, further comprising a cover configured to be secured to the neck over the insert.

20. The waste container of claim 13, further comprising a deactivating agent positioned within the container and indicia on the container and indicative of a fill line to which water should be added to the container, through the insert in the opening, to actuate the deactivating agent for use.

* * * * *